United States Patent [19]

Gibson

[11] 4,105,854

[45] Aug. 8, 1978

[54] PROSTANOIC ACID DERIVATIVES

[75] Inventor: Keith Hopkinson Gibson, Macclesfield, England

[73] Assignee: Imperial Chemical Industries Limited, London, England

[21] Appl. No.: 563,454

[22] Filed: Mar. 31, 1975

[30] Foreign Application Priority Data

Apr. 22, 1974 [GB] United Kingdom ............. 17497/74

[51] Int. Cl.$^2$ .............................................. C07C 177/00
[52] U.S. Cl. ........................................ 560/55; 560/56; 260/520 D; 260/520 R; 424/308; 424/317
[58] Field of Search .......... 260/473 R, 520 D, 520 R; 424/308, 317; 560/55

[56] References Cited

U.S. PATENT DOCUMENTS

| 3,879,437 | 4/1975 | Axen | 560/121 |
|---|---|---|---|
| 3,879,439 | 4/1975 | Axen | 560/121 |

Primary Examiner—Paul J. Killos
Attorney, Agent, or Firm—Cushman, Darby & Cushman

[57] ABSTRACT

This application describes novel 17-(optionally substituted)phenyl-18,19,20-trinorprosta-16-ynoic acid derivatives of the F, E and A series, for example methyl 9α,11α,15-trihydroxy-17-phenyl-18,19,20-trinorprosta-5-cis,13-trans-dien-16-ynoate, together with processes for their manufacture, pharmaceutical or veterinary compositions containing them, and a method of luteolysis in a mammalian host.

7 Claims, No Drawings

PROSTANOIC ACID DERIVATIVES

This invention relates to new prostanoic acid derivatives, and in particular it relates to new prostanoic acid derivatives which possess luteolytic activity. The new compounds are therefore advantageous when used as contraceptives or for the induction of labour, or for control of the oestrus cycle in animals. The compounds may also be useful for early termination of pregnancy, as hypotensives, for the relief of bronchospasm, and as inhibitors of blood platelet aggregation or of gastric secretion.

According to the invention there is provided a prostanoic acid derivative of the formula:

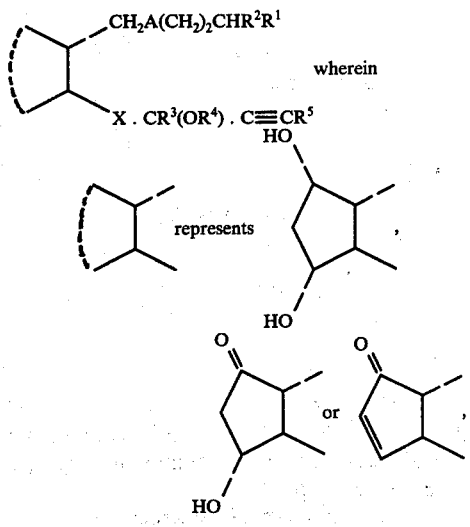

wherein $R^1$ is a carboxy or hydroxymethyl radical, or an alkoxycarbonyl or alkoxymethyl radical of 2 to 12 carbon atoms, $R^2$, $R^3$ and $R^4$ are each a hydrogen atom or an alkyl radical of 1 to 5 carbon atoms, A is an ethylene or vinylene radical, X is an ethylene or trans-vinylene radical, and $R^5$ is a phenyl or naphthyl radical which is unsubstituted or is substituted by alkyl, alkoxy or halogenoalkyl radicals each of 1 to 5 carbon atoms, halogen atoms, or hydroxy or tetrahydropyran-2-yloxy radicals, and for those compounds wherein $R^1$ is a carboxy radical, the pharmaceutically or veterinarily acceptable base addition salts thereof.

A suitable value for $R^1$ when it is an alkoxycarbonyl radical of 2 to 12 carbon atoms is, for example, a methoxycarbonyl, ethoxycarbonyl, butoxycarbonyl or n-decyloxycarbonyl radical, more particularly an alkoxycarbonyl radical of 2 to 5 carbon atoms, and a suitable value for $R^1$ when it is an alkoxymethyl radical of 2 to 12 carbon atoms is, for example, a methoxymethyl, ethoxymethyl, butoxymethyl or n-decyloxymethyl radical, more particularly an alkoxymethyl radical of 2 to 5 carbon atoms.

A suitable value for any one of $R^2$, $R^3$ or $R^4$ when it is an alkyl radical is, for example a methyl or ethyl radical.

A suitable value for a halogen substituent in $R^5$ is, for example, a chlorine, bromine, iodine or fluorine atom, especially a chlorine or fluorine atom, a suitable halogenoalkyl radical is, for example, a fluoroalkyl radical, especially a trifluoromethyl radical, and a suitable value for an alkyl or alkoxy substituent in $R^5$ is, for example, an alkyl or alkoxy radical of 1 or 2 carbon atoms, particularly a methyl or methoxy radical. The radical $R^5$ preferably contains not more than two such substituents.

A suitable pharmaceutically or veterinarily acceptable base addition salt is, for example, an ammonium, alkylammonium containing 1 to 4 alkyl radicals each of 1 to 6 carbon atoms, alkanolammonium containing 1 to 3 2-hydroxyethyl radicals, or alkali metal salt, for example a triethylammonium, ethanolammonium, diethanolammonium, sodium or potassium salt.

It will be observed that the compounds of the formula I contain at least three asymmetric carbon atoms, namely the two carbon atoms at which the side-chains are attached to the ring (the relative stereochemistry at these two carbons is fixed), and the carbon atom of the group $CR^3(OR^4)$ in the lower side chain. In addition, three other carbon atoms may be asymmetrically substituted, so that it is clear that all compounds of the invention may exist in at least two optically active forms. It is to be understood that the useful properties of racemates described in this specification may be present to differing extents in the optical isomers, and that this invention relates to the racemic form of compounds of the formula I and to any optically active form which shows the same useful properties, it being a matter of common general knowledge how the optically active forms may be obtained and their biological properties determined. It is also to be understood that the invention relates to both C-15 epimers, that is, epimers at the $CR^3(OR^4)$ carbon atom of the lower side-chain.

In a preferred group of compounds, $R^1$ is a carboxy, hydroxymethyl or methoxycarbonyl radical, $R^2$ and $R^4$ are hydrogen atoms, $R^3$ is a hydrogen atom or a methyl radical, and $R^5$ is a phenyl radical which is unsubstituted or is substituted by one chlorine or fluorine atom, or a methyl, methoxy, trifluoromethyl, hydroxy or tetrahydropyran-2-yloxy radical, and a particularly preferred group comprises those compounds wherein $R^5$ is a phenyl, 2-,3- or 4-chlorophenyl, 2-, 3- or 4-fluorophenyl, 3-trifluoromethylphenyl, 2- or 3-tolyl, 3-hydroxyphenyl or 3-(tetrahydropyran-2-yloxy)phenyl radical.

Further preferred groups comprise those compounds wherein $R^1$ is a carboxy or alkoxycarbonyl radical as defined above, those compounds wherein $R^1$ is a hydroxymethyl radical and those compounds wherein $R^1$ is an alkoxymethyl radical as defined above, each in combination with any of the definitions of $R^5$ given above.

Further preferred groups comprise those compounds wherein $R^2$ and $R^4$ are each a hydrogen atom and $R^3$ is a hydrogen atom or a methyl radical, in combination with any of the definitions of $R^5$ and $R^1$ given above.

Further preferred groups comprise those compounds wherein A is an ethylene or cis-vinylene radical, each in combination with any of the definitions of $R^5$, $R^1$ and $R^2$, $R^3$ and $R^4$ given above.

Further preferred groups comprise those compounds wherein X is an ethylene or trans-vinylene radical, each in combination with any of the definitions of $R^5$, $R^1$, $R^2$, $R^3$, $R^4$ and A given above.

Further preferred groups comprise those compounds wherein

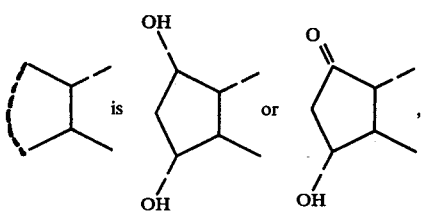

each in combination with any of the definitions of $R^5$, $R^1$, $R^2$, $R^3$ and $R^4$, A and X given above.

Particular preferred compounds of the invention are 9α,11α,15-trihydroxy-17-phenyl-18,19,20-trinorprosta-5-cis,13-trans-dien-16-ynoic acid, methyl 9α,11α,15-trihydroxy 17-phenyl-18,19,20-trinorprosta-5-cis,13-trans-dien-16-ynoate, 17-(3-fluorophenyl)-9α,11α,15-trihydroxy-18,19,20-trinorprosta-5-cis,13-trans-dien-16-ynoic acid, 17-(3-fluorophenyl)-9α,11α,15-trihydroxy-15-methyl-18,19,20-trinorprosta-5-cis,13-trans-dien-16-ynoic acid, 17-(4-fluorophenyl)-9α,11α,15-trihydroxy-18,19,20-trinorprosta-5-cis,13-trans-dien-16-ynoic acid, 9α,11α,15-trihydroxy-17-(2-tolyl)-18,19,20-trinorprosta-5-cis,13-trans-dien-16-ynoic acid, 9α,11α,15-trihydroxy-17-(3-hydroxyphenyl)-18,19,20-trinorprosta-5-cis,13-trans-dien-16-ynoic acid, 9α,11α,15-trihydroxy-17-[3-(tetrahydropyran-2-yloxy)phenyl]-18,19,20-trinorprosta-5-cis,13-trans-dien-16-ynoic acid, 17-(2-chlorophenyl)-9α,11α,15-trihydroxy-18,19,20-trinorprost-5-cis,13-trans-dien-16-ynoic acid, 9α,11α,15-trihydroxy-17-(3-trifluoromethylphenyl)-18,19,20-trinorprosta-5-cis,13-trans-dien-16-ynoic acid, 9α,11α,15-trihydroxy-17-(3-tolyl)-18,19,20-trinorprost-5-cis,13-trans-dien-16-ynoic acid, and 17-(3-fluorophenyl)-9α,1α,15-trihydroxy-18,19,20-trinorprost-5-cis-en-16-ynoic acid, especially the first-named four compounds.

The new prostanoic acid derivatives of the invention may be manufactured by methods known in themselves for the manufacture of chemically analogous compounds. Thus, the following processes are provided as further features of the invention:

(a) for those compounds wherein

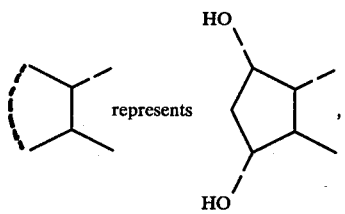

$R^1$ is a carboxy radical and $R^3$ and $R^4$ are each a hydrogen atom, the hydrolysis under basic conditions of a compound of the formula:

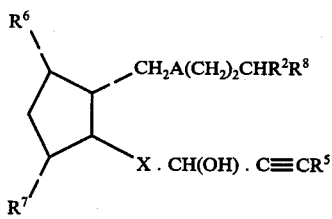

II wherein $R^2$, $R^5$, A and X have the meanings stated above, $R^6$ is an aroyloxy radical of up to 15 carbon atoms, for example a 4-phenylbenzoyloxy radical, $R^7$ is a hydroxy radical or an aroyloxy radical of up to 15 carbon atoms, for example a 4-phenylbenzoyloxy radical, and $R^8$ is an alkoxycarbonyl radical of 2 to 12 carbon atoms, for example a methoxycarbonyl radical, for example using potassium carbonate or potassium hydroxide in a solvent, whereafter if a salt is required the product is reacted with a base; or (b) for those compounds wherein

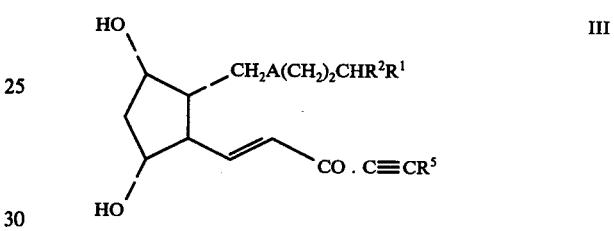

and $R^3$ and $R^4$ are each a hydrogen atom, the reduction of an enone of the formula:

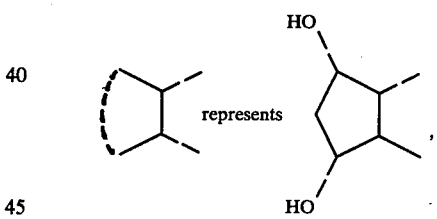

III wherein $R^1$, $R^2$, $R^5$, A have the meanings stated above, with, for example, zinc borohydride, aluminium tri-isopropoxide, di-isobornyloxy aluminum isopropoxide or sodium borohydride; or (c) for those compounds wherein

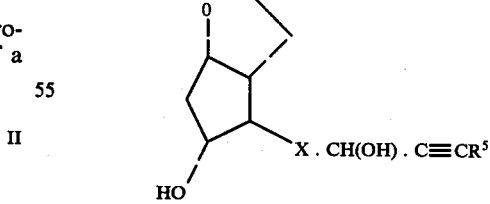

$R^1$ is a carboxy radical, and $R^3$ and $R^4$ are each a hydrogen atom, the reaction of a lactol of the formula:

IV wherein $R^5$ and X have the meanings stated above, with a phosphonium salt of the formula $(C_6H_5)_3P^+O.(CH_2)_3CHR^2COOH.Br^-$ wherein $R^2$ has the meanings stated above, in the presence of a strong base, for example butyl-lithium or methanesulphinylmethyl sodium, whereafter if a salt is required the product is reacted with a base; or (d) for those compounds wherein

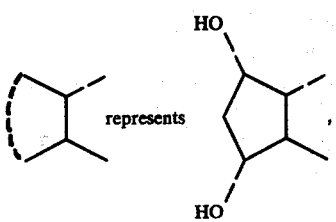

the reduction of the corresponding compound of the invention wherein

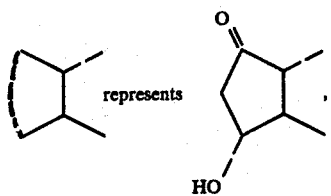

for example with a complex metal hydride, for example a lithium tri(lower alkyl) hydride such as lithium tri-s-butyl hydride, or a borohydride such as sodium borohydride; or (e) for those compounds wherein

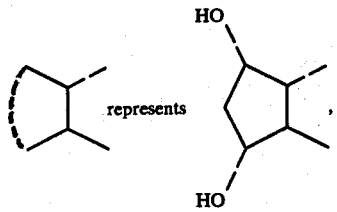

$R^1$ is a carboxy or alkoxycarbonyl radical, $R^3$ is an alkyl radical and $R^4$ is a hydrogen atom, the reaction of an enone of the formula III wherein $R^2$, $R^5$ and A have the meanings stated above and $R^1$ has the meaning stated immediately above, with an equivalent amount of an alkyl magnesium halide containing 1 to 5 carbon atoms, for example an alkyl magnesium bromide or iodide; or (f) for those compounds wherein

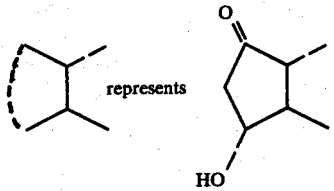

and $R^3$ is an alkyl radical, the oxidation of a compound of the formula:

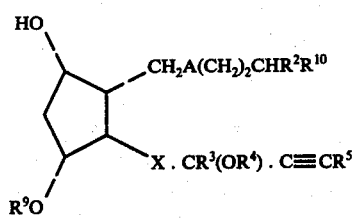
V wherein $R^2$, $R^5$ and A have the meanings stated above, $R^3$ has the meaning stated immediately above, $R^4$ is an alkyl radical or a radical of the formula $R^9$, $R^9$ is a trialkylsilyl radical, for example a dimethyl-t-butylsilyl radical and $R^{10}$ is an alkoxycarbonyl radical or a trialkylsilyloxycarbonyl radical, for example a dimethyl-t-butylsilyloxycarbonyl radical, with for example chromium trioxide/pyridine complex in methylene dichloride; or (g) for those compounds wherein $R^4$ is an alkyl radical, the reaction of a compound of the formula I wherein $R^4$ is a hydrogen atom with an alkyl halide, for example an alkyl iodide, in the presence of a strong base, for example sodium hydride; or (h) for those compounds wherein $R^1$ is an alkoxycarbonyl radical, the reaction of a prostanoic acid derivative of the formula I, wherein $R^1$ is a carboxy radical, with a diazoalkane of 1 to 11 carbon atoms, or of a salt thereof, for example a sodium or silver salt, with an alkyl halide of 1 to 11 carbon atoms, for example an alkyl iodide or alkyl bromide; or (i) for those compounds wherein $R^1$ is a hydroxymethyl radical, the hydrolysis of a compound of the formula:

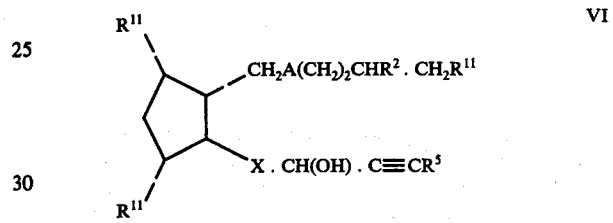
VI wherein $R^2$, $R^5$, A and X have the meanings stated above, and $R^{11}$ is an aroyloxy radical of up to 15 carbon atoms, for example a 4-phenylbenzoyloxy radical, with for example, an alkali metal carbonate, for example potassium carbonate in methanol; or (j) for those compounds wherein A is a trans-vinylene radical, the separation of a mixture of a compound of the formula I wherein A is a cis-vinylene radical and the corresponding compound of the formula I wherein A is a trans-vinylene radical, by conventional means, for example by fractional crystallisation or by chromatography; or (k) for those compounds wherein $R^1$ is a carboxy or hydroxymethyl radical, and

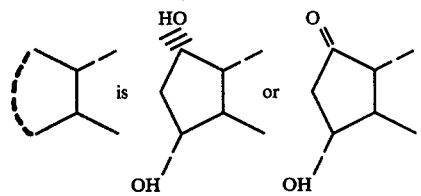

the hydrolysis of a tetrahydropyranyl ether of the formula:

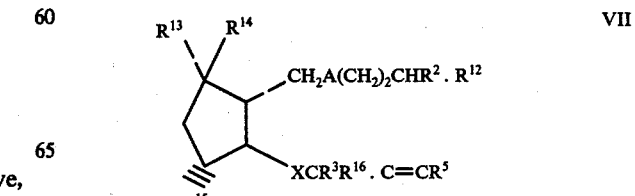
VII wherein $R^2$, $R^3$, $R^5$, A and X have the meanings defined above, $R^{12}$ is a carboxy or hydroxymethyl radical, $R^{13}$ is a hydroxy or tetrahydropyran-2-yloxy radical and $R^{14}$ is a hydrogen atom or $R^{13}$ and $R^{14}$ together form an oxo radical, and $R^{15}$ and $R^{16}$ are each a hydroxy or tetrahydropyran-2-yloxy radical, provided that the compound VII contains at least one tetrahydropyran-2-yloxy radical, with an acid, for example acetic acid; or (1) for those compounds wherein

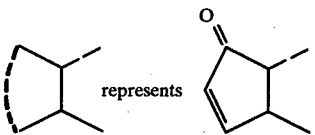

the dehydration of a compound of the formula I wherein

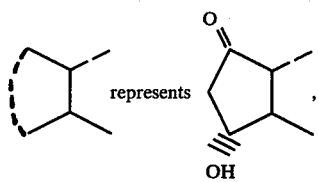

for example with a substituted carbodi-imide in the presence of a copper salt, for example N,N¹-dicyclohexylcarbodi-imide in the presence of cupric chloride.

A starting material of the formula II wherein A is a cis-vinylene radical, $R^6$ is a 4-phenylbenzoyloxy radical, $R^7$ is a hydroxy radical, $R^8$ is a methoxycarbonyl radical and $R^2$ is a hydrogen atom may be obtained by reacting the known ester, methyl 7-[2β-formyl-3α-hydroxy-5α-(4-phenylbenzoyloxy)cyclopent-1α-yl]hept-5-cis-enoate (VIII) with a phosphonate $(CH_3O)_2PO.CH_2\text{-}COC{\equiv}CR^5$ in the presence of a strong base, or a phosphorane $Ph_3P{:}CHCOC{\equiv}CR^5$, to give an enone IX which, on reduction with zinc borohydride, aluminium tri-isopropoxide or di-isobornyloxy aluminium isopropoxide, gives the required starting material II.

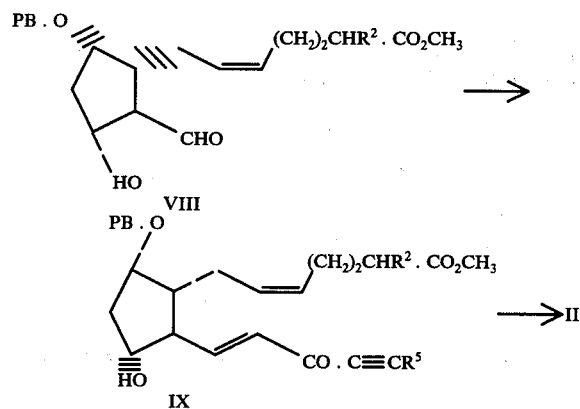

PB = 4-phenylbenzoyl.

Starting materials of the formula II wherein $R^6$ is an aryloxy radical other than 4-phenylbenzoyloxy or wherein $R^8$ is other than a methoxycarbonyl radical, and wherein $R^7$ is a hydroxy radical and $R^2$ is a hydrogen atom, may be prepared similarly from suitable analogues of the ester VIII, which analogues are prepared in a completely analogous manner to VIII itself.

Starting materials of the formula II wherein $R^7$ is a hydroxy radical and $R^2$ is an alkyl radical may be prepared similarly from analogues of VIII containing an alkyl substituent on the carbon atom α to the methyl ester, which analogues are prepared in a completely analogous manner to VIII itself.

Starting materials of the formula II wherein $R^7$ is a hydroxy radical and A is an ethylene radical may be prepared in a similar manner from the known ester, methyl 7-[2β-formyl-3α-hydroxy-5α-(4-phenylbenzoyloxy)cyclopent-1α-yl]heptanoate, from analogous higher alkyl esters, and from analogues containing an alkyl substituent on the carbon atom α to the methyl ester.

Starting materials of the formula II wherein $R^7$ is a hydroxy radical and X is an ethylene radical may be obtained by carrying out the reduction of the enone IX, or an analogue thereof, wherein A is an ethylene radical, or which contains an alkyl substituent on C-2, with sodium borohydride.

Starting materials of the formula II wherein $R^7$ is an aroyloxy radical may be prepared similarly from the known esters, methyl 7-[β-formyl-3α,5α-di(4-phenylbenzoyloxy)cyclopent-1α-yl]hept-5-cis-enoate, and the corresponding heptanoate, or from analogues thereof of the formula II wherein $R^2$ is an alkyl radical, $R^6$ and $R^7$ are aroyloxy radicals other than 4-phenylbenzoyloxy radicals or $R^8$ is an alkoxycarbonyl radical other than a methoxycarbonyl radical, which analogues are prepared in a completely analogous manner to the known esters.

A starting material of the formula III wherein $R^1$ is a methoxycarbonyl radical, $R^2$ is a hydrogen atom and A is a cis-vinylene radical may be obtained from the known ester, methyl 7-[2β-formyl-3α,5α-dihydroxycyclopent-1α-yl]hept-5-cis-enoate, by reaction with a phosphonate in the manner described above for similar compounds. Other starting materials III wherein $R^2$ is an alkyl radical may be obtained similarly from the appropriate analogues of the known ester, which analogues are prepared in a completely analogous manner to the known ester. Starting materials III wherein A is an ethylene radical may be obtained similarly from analogues of the known ester wherein A is an ethylene radical, which analogues may be prepared similarly to the known ester, but starting with a hydrogenated precursor.

Lactols of the formula IV, wherein X is a trans-vinylene radical, used as starting materials in process (c) of the invention, may be obtained by reaction of the known aldehyde X, (Ac = acetyl or 4-phenylbenzoyl) with a phosphonate of the formula $(CH_3O)_2PO.CH_2\text{-}CO.C{\equiv}CR^5$ or a phosphorane of the formula $Ph_3P{:}CHCO.C{\equiv}CR^5$ to give an enone XI. The enone XI is reduced with zinc borohydride, aluminium tri-isopropoxide or di-isobornyloxy aluminium isopropoxide to the corresponding enol XII, the protecting acyl group is hydrolysed with potassium carbonate in methanol to the lactone XIII, and the lactone XIII is reduced with di-isobutyl aluminium hydride to the required lactol IV.

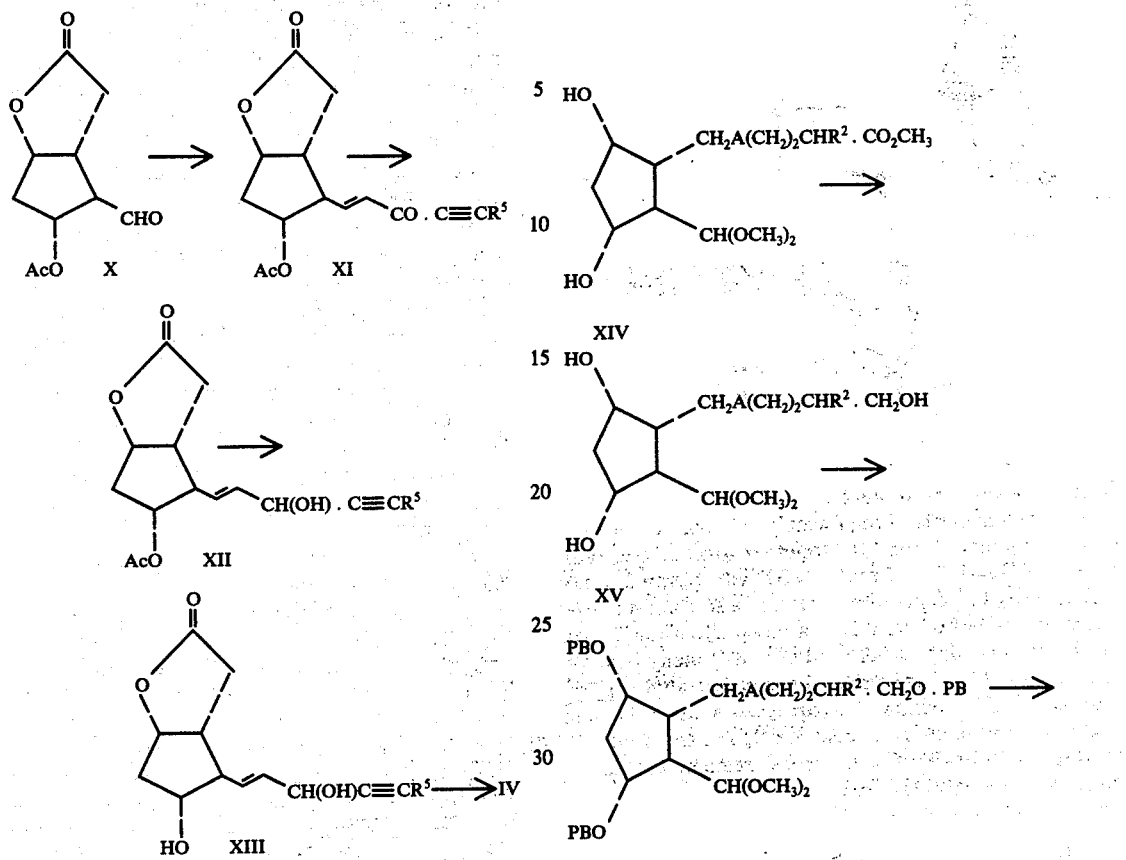

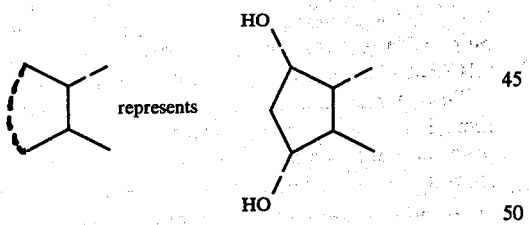 represents $R^1$ is a carboxy or alkoxycarbonyl radical and $R^3$ is an alkyl radical, with for example a trialkylsilyl amide, for example (diethylamino) dimethyl-t-butylsilane.

Lactols of the formula IV wherein X is an ethylene radical may be prepared similarly, using sodium borohydride for the reduction of the enone XI.

The starting material of the formula V may be obtained by selective silylation of a compound of the invention of the formula I wherein The starting material of the formula VI may be prepared by lithium aluminium hydride reduction of the diol XIV to a triol XV, which is protected as the tris(4-phenylbenzoate ester) XVI. The acetal group is selectively hydrolysed to the aldehyde XVII, which is reacted with a phosphonate or phosphorane as described above to give the enone XVIII, reduction of which, for example with di-isobornyloxy aluminium isopropoxide, gives the starting material VI.

The corresponding starting materials VI wherein A is ethylene may be obtained by the general methods described above.

The mixture of compounds wherein A is cis-vinylene and compounds wherein A is trans-vinylene used as the starting material for process (j) above may be obtained

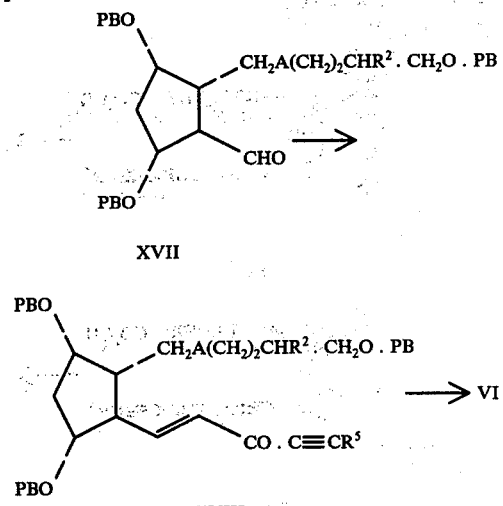

PB = 4-phenylbenzoyl by using n-butyl-lithium as the strong base in the reaction of the known lactol XIX with a phosphorane in sulpholane to give a mixture of cis and trans isomers of the compound XX. The cis-trans mixture of compound XX is then converted to the required cis-trans starting material in the same way as it is known to convert the cis compound XX to the corresponding cis-compound of the formula I.

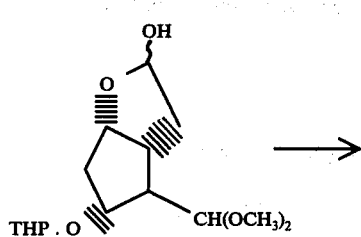

XIX

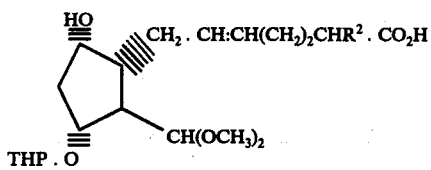

XX

THP = tetrahydropyran-2-yl.

Starting materials of the formula VII wherein $R^{12}$ is a carboxy radical, $R^{13}$ and $R^{14}$ together form an oxo radical, and $R^{15}$ and $R^{16}$ are each a tetrahydropyran-2-yloxy radical, may be prepared by reacting a starting material of the formula II wherein $R^8$ is a methoxycarbonyl radical, $R^7$ is a hydroxy radical and $R^6$ is a 4-phenylbenzoyl radical with dihydropyran to give a bis(tetrahydropyranyl ether) XXI, which is hydrolysed with potassium hydroxide to the hydroxy-acid XXII, and the hydroxy-acid XXII is oxidised with Jones' reagent to the required starting material VII.

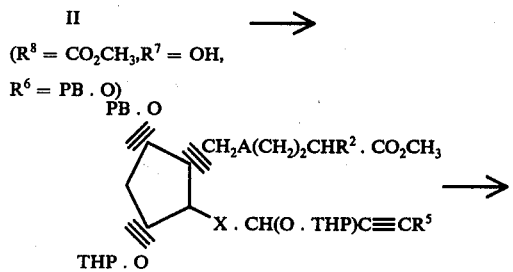

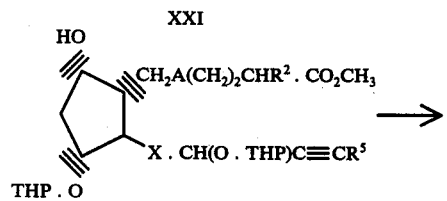

XXII

VII

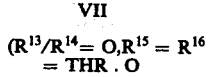

THP = tetrahydropyran-2-yl
PB = 4-phenylbenzoyl

Starting materials of the formula VII wherein $R^{12}$ is a hydroxymethyl radical, $R^{14}$ is a hydrogen atom and $R^{13}$, $R^{15}$ and $R^{16}$ are each a tetrahydropyran-2-yloxy radical may be prepared from a compound of the invention of the formula I wherein $R^1$ is a carboxy or alkoxycarbonyl radical by reaction thereof with 2,3-dihydropyran to give respectively a tetrakis- or tris- tetrahydropyranyl derivative, which is reduced with lithium aluminium hydride to the required starting material VII.

It is, of course, to be understood that an optically active compound of the invention may be obtained either by resolving the corresponding racemate, or by carrying out the above-described reaction sequences starting from an optically active intermediate.

As stated above, the compounds of the invention possess luteolytic properties, and in particular they are more active as luteolytic agents and less active as smooth muscle stimulants than the naturally occurring prostaglandins. Thus, for example, the mixed C-15 epimers methyl 9α,11α,15-trihydroxy-17-phenyl 18,19,20-trinorprosta-5-cis,13-trans-dien-16-ynoate is approximately 50-100 times as active as natural prostaglandin F$_2$α as a luteolytic agent in hamsters (subcutaneous dosing) but possesses only approximately one tenth the smooth muscle stimulant activity. No indication of mammalian toxicity has been noted at minimum luteolytically effective doses with any of the exemplified compounds.

When a compound of the invention is to be used for the induction of labour, it is used in the same way as it is known to use the naturally occurring prostaglandin E$_2$, that is by administering a sterile, substantially aqueous solution containing from 0.01 to 10 μg./ml., preferably 0.01 to 1 μg./ml. of the compound, by intravenous infusion, or by transcervical extra-amniotic or intra-amniotic infusion until labour commences. Also, for this purpose, the compounds of the invention may be used in combination, or concurrently, with a uterine stimulant, for example oxytocin, in the same way as it is known to use the natural prostaglandins in combination, or concurrently, with oxytoxin for the induction of labour.

When a compound of the invention is to be used for control of the oestrus cycle in animals, for example cattle or horses, it is used in the same way as it is known to use the prostaglandin derivatives known as I.C.I. 80996 and I.C.I. 81008 ('Equimate' — trade mark) for this purpose. The compounds may be used for this purpose in combination, or concurrently, with a gonadotrophin, for example pregnant mare serum gonadotrophin (PMSG) or human chorionic gonadotrophin (HCG) to hasten the onset of the next cycle.

Thus, according to a further feature of the invention there is provided a pharmaceutical or veterinary composition comprising a prostanoic acid derivative of the formula I together with a pharmaceutically or veterinarily acceptable diluent or carrier.

The compositions may be in a form suitable for oral administration, for example tablets or capsules, in a form suitable for inhalation, for example an aerosol or a solution suitable for spraying, in a form suitable for infusion, for example sterile, substantially aqueous, or oil, solutions or suspensions, or in the form of a suppository, suitable for anal or vaginal use.

The compositions of the invention may be prepared by conventional means, and may contain conventional excipients.

The invention is illustrated, but not limited, by the following Examples. Throughout the examples R$_F$ values refer to silica gel plates supplied commercially by Merck of Darmstadt, and the spots were visualised either by fluorescence under ultraviolet radiation, by exposure to iodine vapour, or by spraying the plates with a solution of ceric ammonium nitrate in sulphuric acid and heating. Organic solutions were dried with anhydrous magnesium sulphate.

EXAMPLE 1

A solution of the enol, methyl 15-hydroxy-17-phenyl-9α,11α-di(4-phenylbenzoyloxy)-18,19,20-trinorprosta-5-cis, 13-trans-dien-16-ynoate (58 mg.) in anhydrous methanol (2.5 ml.) and methylene dichloride (1 ml.) was stirred with powdered anhydrous potassium carbonate (40 mg.) for 66 hours at room temperature under argon. The solution was filtered, and the filtrate was purified by thin layer chromatography on silica gel, eluting with ethyl acetate, to give the C-15 epimers of methyl 9α,11α,15-trihydroxy-17-phenyl-18,19,20-trinorprosta-5-cis, 13-trans-dien-16-ynoate, $R_F = 0.20$ and $0.27$. The n.m.r. spectrum in deuteriochloroform showed the following characteristic absorptions (δ values):

7.2 – 7.6, 5H, multiplet, aromatic protons,
5.76 – 5.9, 2H, trans-olefinic protons,
5.2 – 5.7, 2H, cis-olefinic protons,
5.1, 1H, C-15 proton.

The mass spectrum for the tri(trimethylsilyl) derivative showed $M^+ = 614.3279$ (calculated for $C_{33}H_{54}O_5$. $Si_3 = 614.3279$).

The enol used as starting material in the above process may be prepared as follows:

N-Butyl-lithium (13.5 ml. of a 2.29 M solution in hexane) was added dropwise to a stirred solution of dimethyl methylphosphonate (3.84 g.) in anhydrous tetrahydrofuran (25 ml.) at $-78°$ under argon. After 15 minutes, a solution of ethyl phenylpropiolate (2.5 g.) in anhydrous tetrahydrofuran (20 ml.) was added. The reaction mixture was stirred for 2 hours at $-78°$ C., allowed to warm to ambient temperature and stirred for 18 hours, and adjusted to pH 5 by addition of glacial acetic acid. The tetrahydrofuran was evaporated at room temperature under reduced pressure and the residue was partitioned between water and diethyl ether. The diethyl ether layer was separated, washed with water and dried, and the solvent was evaporated. Chromatography of the crude product on silica gel MFC (75 g.)., eluting with diethyl ether/ethyl acetate (9:1), gave unreacted ethyl phenylpropiolate, and subsequent elution with diethyl ether/ethyl acetate (1:1), gave dimethyl 2-oxo-4-phenylbut-3-ynylphosphonate as an oil, $R_F = 0.28$ (ethyl acetate). The n.m.r. spectrum in deuteriochloroform showed the following absorptions (δ values):

3.45, 2H, doublet, $\equiv P-C\underline{H}_2CO-$
3.90, 6H, doublet, $-CH_2PO(OC\underline{H}_3)_2$
7.3 – 7.8, 5H, aromatic protons.

1N aqueous sodium hydroxide (0.6 ml.) was added to a solution of dimethyl 2-oxo-4-phenylbut-3-ynyl phosphonate (265 mg.) and methyl 7-[2β-formyl-3α,5α-di(4-phenylbenzoyloxy)cyclopent-1α-yl]hept-5-cis-enoate (195 mg.) in a mixture of toluene (10 ml.) and 2-methylpropan-2-ol (2 ml.) under argon at 0° C., and the solution was stirred vigorously at ambient temperature for 66 hours. Glacial acetic acid was added to give pH 4.5. The mixture was partitioned between ethyl acetate and brine, the ethyl acetate solution was separated, washed with more brine and dried, and the solvents were evaporated. Preparative layer chromatography of the residue on silica gel, eluting with ethyl acetate/toluene (15:85), gave (after extraction) the enone, methyl 15-oxo-17-phenyl-9α,11α-di(4-phenylbenzoyloxy)-18,19,20-trinorprosta-5-cis,13-trans-dien-16-ynoate, as an oil $R_F = 0.48$ (85:15 toluene/ethyl acetate). The n.m.r. spectrum in deuteriochloroform showed the following characteristic absorptions (δ values):

3.53, 3H, singlet, $-CO_2C\underline{H}_3$
5.2–5.6, 4H, multiplet, cis-olefinic, C-9 and C-11 protons,
6.4, 1H, doublet, C-14 proton A solution of the enone (155 mg.) in dry toluene (7 ml.) was stirred at room temperature under argon, and treated with di-isobornyloxyaluminum isopropoxide (1.71 ml. of a 0.36M solution in toluene). After 20 hours, the solution was partitioned between ethyl acetate and brine, the organic layer was separated, washed with brine and dried, and the solvent was evaporated. The residue was twice triturated with pentane (2 × 10 ml.), to remove isoborneol and leave the petrol insoluble, required enol, methyl 15-hydroxy-17-phenyl-9α,11α-di-(4-phenylbenzoyloxy)-18,19,20-trinorprosta-5-cis,13-trans-dien-16-ynoate, a viscous oil, $R_F = 0.24$ (85:15 toluene/ethyl acetate).

The methyl 7-[2β-formyl-3α,5α-di-(4-phenylbenzoyloxy)-cyclopent-1α-yl]hept-5-cis-enoate used in the above process may be prepared as described in Belgian Pat. No. 807,161.

EXAMPLE 2

To a solution of crude methyl 17-(3-fluorophenyl)-15-hydroxy-9α,11α-di(4-phenylbenzoyloxy)-18,19,20-trinor-prosta-5-cis-13-trans-dien-16-ynoate in methanol (10 ml.) and dimethoxyethane (5 ml.) was added a solution of potassium hydroxide (400 mg.) in water (2 ml.), and the mixture was stirred for 18 hours. The pH of the mixture was then adjusted to 5 and the mixture was extracted with ethyl acetate. The extracts were washed with brine, then dried (magnesium sulphate) and the solvent was evaporated. The residue was purified by thin layer chromatography on silica gel, by elution with 3% acetic acid in ethyl acetate, to give the C-15 epimers of 17-(3-fluorophenyl)-9α,11α,15-trihydroxy-18,19,20-trinorprosta-5-cis-13-trans-dien-16-ynoic acid, $R_F = 0.50$ and $0.56$ (3% acetic acid in ethyl acetate). The mass spectrum showed $M^+ = 690.3432$ (calculated for $C_{35}H_{59}O_5Si_4F = 690.3425$). The n.m.r. spectrum in deuteroacetone showed the following characteristic absorptions (δ values).

| | |
|---|---|
| 6.9 – 7.5, 4H, multiplet aromatic protons | |
| 5.7 – 5.86, multiplet, trans-olefinic protons | |
| 5.14 – 5.7, multiplet, cis-olefinic protons | |
| 5.02 – 5.1, multiplet, C-15 proton | 11 protons, |
| 3.82 – 4.22, multiplet, C-9 and C-11 protons | |
| 3.7 – 5.9, broad hump, 4 × —OH | |

The starting material for the above process was prepared by repeating the process described in Example 1 using ethyl-3-fluorophenylpropiolate instead of ethyl phenylpropiolate to give:

dimethyl 4-(3-fluorophenyl)-2-oxobut-3-ynylphosphonate, [$R_F = 0.33$ (ethyl acetate). The n.m.r. spectrum in deuteriochloroform showed the following characteristic peaks (δ values).

| | |
|---|---|
| 7.0 – 7.45, | 4H, multiplet, aromatic protons, |
| 3.8, | 6H, doublet (J = 12 Hz), 2 × $\overset{\overset{\text{O}}{\|}}{P}-OC\underline{H}_3$ |

-continued 3.35, 2H, doublet (J = 22 Hz), —COCH$_2$P⟨ ]

and the corresponding enone, methyl 17-(3-fluorophenyl)-15-oxo-9α,11α-di(4-phenylbenzoyloxy)-18,19,20-trinorprost-5-cis,13-trans-dien-16-ynoate [R$_F$ = 0.58 (15% ethyl acetate in toluene). The n.m.r. spectrum in deuteriochloroform showed the following characteristic peaks (δ values):

7.0 – 8.25, 23 protons, multiplet, aromatics plus C-13 proton,
6.42, — 1 proton, doublet (J = 16 Hz), C-14 proton,
5.2 – 5.6, 4H, multiplet, cis-olefinic protons, C-9 proton and C-11 proton,
3.52, 3H, singlet, —CO$_2$CH$_3$]

In a similar manner, using the appropriate propiolic ester as starting material, the following prostanoic acid derivatives of the formula XXIII were prepared, via the phosphonates of the formula XXIV and the enones of the formula XXV:

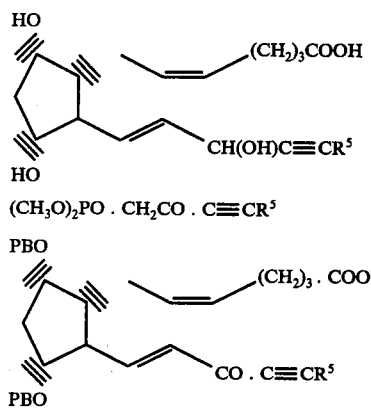

ynoic acid, R$_F$ = 0.35 and 0.43 (3% acetic acid in ethyl acetate). The n.m.r. spectrum of the more polar C-15 epimer, in deuterated acetone, showed the following characteristic absorptions (δ values):

6.8 –7.3, 4H, multiplet, aromatic protons,
5.6 – 5.75,2H, multiplet, trans-olefinic protons,
4.9 –5.05, 1H, C-15 proton,
3.75, 3H, singlet, —O.CH$_3$, The mass spectrum for the tetra(trimethylsilyl) derivative showed M$^+$=704.3809 (calculated for C$_{36}$H$_{64}$O$_6$Si$_4$=704.3780).

The methyl 11α,15-dihydroxy-17-(3-methoxyphenyl)-9α-(4-phenylbenzoyloxy)-18,19,20-trinorprosta-13-trans-en 16-ynoate used as starting material in the above process may be prepared as follows:

Dimethyl 4-(3-methoxyphenyl)-2-oxobut-3-ynylphosphonate (386 mg., 2 equivalents) and methyl 7-[2β-formyl-3α-hydroxy-5α-(4-phenylbenzoyloxy)-cyclopent-1α-yl]-heptanoate (357 mg. 1 equivalent) were suspended under argon in a mixture of toluene (12 ml.) and t-butanol (2 ml.). Aqueous 1M sodium hydroxide solution (1.125 ml., 1.5 equivalents) was added and the two phase mixture was stirred vigorously for 2 hours. The reaction mixture was shaken with ethyl acetate and saturated brine, and the organic layer was separated. The aqueous layer was extracted with ethyl acetate, the combined organic extracts were dried, and the solvent was evaporated. Preparative thin layer chromatography gave methyl 11α-hydroxy-17-(3-methoxyphenyl)-15-oxo-9α-(4-phenylbenzoyloxy)-18,19,20-trinorprosta-13-trans-en-16-ynoate as a clear oil, R$_F$ = 0.7 (15% ethyl acetate in toluene) whose n.m.r. spectrum in deuteriochloroform showed the following character characteristic absorptions (δvalues):

6.9 –8.2, 14H, multiplet, aromatic and C-13 protons,
6.44, 1H, doublet, (J=15Hz), C-14 proton,
3.81, 3H, singlet, —OCH$_3$,
3.58, 3H, singlet, —CO$_2$CH$_3$ The process described in the latter part of Example 1 was repeated using methyl 11α-hydroxy-17-(3-methox-

| R$^5$ | Mass spectrum, M$^{+(a)}$ | | R$_F^{(b)}$ | Phosphonate R$_F^{(c)}$ | Enone R$_F^{(d)}$ |
| --- | --- | --- | --- | --- | --- |
| | Found | Calculated | | | |
| 4-tolyl | 686.3623 | 686.3676 | 0.28/0.42 | 0.41 | 0.49$^{(e)}$ |
| 3-chlorophenyl | 706.3129 | 706.3104 | 0.35/0.42 | 0.41 | 0.70 |
| 2-chlorophenyl | 706.3069 | 706.3104 | 0.49/0.52 | 0.31 | 0.38 |
| 3-trifluromethylphenyl | 740.3384 | 740.3393 | 0.48/0.57 | 0.34 | 0.56 |
| 2,4-dichlorophenyl | 740.2726 | 740.2740 | 0.52 | 0.42 | 0.56 |
| 3-tolyl | 686.3677 | 686.3671 | 0.58/0.66 | 0.41 | 0.55 |
| 2-tolyl | 686.3676 | 686.3671 | 0.45/0.59 | 0.39 | 0.64 |
| 4-fluorophenyl | 690.3398 | 690.3425 | 0.40/0.79 | 0.40 | 0.52 |
| 3-methoxyphenyl | 702.3638 | 702.3624 | 0.29/0.36 | 0.34 | 0.33 |
| 3-tetrahydropyran-2-yloxy)phenyl | 772.4022 | 772.4043 | 0.43/0.50 | 0.29 | 0.40 |
| 2-fluorophenyl | 690.3422 | 690.3425 | 0.48/0.53 | 0.31 | 0.49 |

$^{(a)}$M$^{30}$ for the tetra-(trimethylsilyl) derivative.
$^{(b)}$on silica gel, eluted with 3% acetic acid in ethyl acetate
$^{(c)}$on silica gel, eluted with ethyl acetate
$^{(d)}$on silica gel, eluted with 15% ethyl acetate in toluene
$^{(e)}$on silica gel, eluted with 50% ethyl acetate/toluene.

EXAMPLE 3

The process described in Example 2 was repeated, using methyl 11α,15-dihydroxy-17-(3-methoxyphenyl)-9α-(4-phenylbenzoyloxy)-18,19,20-trinorprosta-13-trans-en-16-ynoate in place of methyl 15-hydroxy-17-(3-fluorophenyl)-9α,11α-di(4-phenylbenzoyloxy)-18.19,20-trinorprosta-5-cis,13-trans-dien-16-ynoate, to give the C-15 epimers of 9α,11α,15-trihydroxy-17-(3-methoxyphenyl)-18,19,20-trinorprosta-13-trans-en-16-yphenyl)-15-oxo-9α-(4-phenylbenzoyloxy)-18,19,20-trinorprosta-13-trans-en-16-ynoate in place of methyl 15-oxo-17-phenyl-9α,11α-di-(4-phenylbenzoyloxy)-18,19,20-trinorprosta-5-cis,13-trans-dien-16-ynoate to give the C-15 epimers of methyl 11α,15-dihydroxy-17-(3-methoxyphenyl)-9α-(4-phenylbenzoyloxy)-18,19,20-trinorprosta-13-trans-en-16-ynoate, R$_F$ = 0.31 (50% ethyl acetate in toluene).

EXAMPLE 4

A solution of 17-(3-fluorophenyl)-9-oxo-11α,15-bis(tetrahydropyran-2-yloxy)-18,19,20-trinorprosta-5-cis,13-trans-dien-16-ynoic acid (30 mg.) in 2.5 ml. of a mixture of 2:1 acetic acid: water was stirred at an ambient temperature for 6 hours, then at 40° C. for 2½ hours. The solvents were evaporated, and the residue contained the mixed C-15 epimers of 17-(3-fluorophenyl)-11α,15-dihydroxy-9-oxo-18,19,20-trinorprosta-5-cis,13-trans-dien-16-ynoic acid, which were separated by thin layer chromatography on silica gel, developing with 3% acetic acid in a 1:1 mixture of ethyl acetate and toluene, $R_F = 0.21$ and $0.28$ The more polar epimer showed the following characteristics:-Mass spectrum of the 9-methoxime-tris(trimethylsilyl) derivative showed $M^+ = 645.3119$ (calculated for $C_{33}H_{52}FO_5NSi_3 = 645.3137$). The n.m.r. spectrum in deuterioacetone showed the following characteristic peaks (δ values):

7.0 – 7.6, 4H, multiplet, aromatic protons
5.8 – 6.0, 2H, multiplet, trans-olefinic protons,
5.34 – 5.5, 2H, multiplet, cis-olefinic protons,
5.11, 1H, doublet, (J = 4Hz), C-15 proton,
4.06 – 4.34, 1H, multiplet, C-11 proton The sequence described in the second part of Example 3 was repeated, using methyl 7-[2β-formyl-3α-hydroxy-5α-(4-phenylbenzoyloxy)cyclopent-1α-yl]hept-5-cis-enoate in place of methyl 7-[2β-formyl-3α-hydroxy-5α-(4-phenylbenzoyloxy)cyclopent-1α-yl]heptanoate, and dimethyl 4-(3-fluorophenyl)-2-oxobut-3-ynylphosphonate in place of dimethyl 4-(3-methoxyphenyl)-2-oxobut-3-ynylphosphonate, to give successively:

methyl 17-(3-fluorophenyl)-11α-hydroxy-15-oxo-9α-(4-phenylbenzoyloxy)-18,19,20-trinorprosta-5-cis, 13-trans-dien-16-ynoate, $R_F = 0.2$ (15% ethyl acetate in toluene); n.m.r. spectrum in deuteriochloroform (δ values):

7.0 – 8.2, 14H, multiplet, aromatic and C-13 protons,
6.46, 1H, doublet (J= 16 Hz), C-14-proton,
5.1–5.6, 4H, multiplet, —O$\underline{H}$, cis-olefinic and C-9 protons,
3.54, 3H, singlet, methyl ester;

methyl 17-(3-fluorophenyl)-11α,15-dihydroxy-9α-(4-phenylbenzoyloxy)-18,19,20-trinorprosta-5-cis,13-trans-dien-16-ynoate, $R_F = 0.17$ and $0.30$ (50% ethyl acetate in toluene);

To a solution of the epimeric diols (115 mg.) of methyl 17-(3-fluorophenyl)-11α,15-dihydroxy-9α-(4-phenylbenzoyloxy)-18,19,20-trinorprosta-5-cis, 13-trans-dien-16-ynoate, in anhydrous toluene (5ml.) at 0° C. under an atmosphere of argon were added successively redistilled 2,3-dihydropyran (0.4 ml.) and a solution of toluene-p-sulphonic acid (0.1 ml. of 1% solution in anhydrous tetrahydrofuran). The solution was stirred at 0° C. for 30 minutes, then 10 drops of pyridine were added, and the solution was washed successively with saturated sodium bicarbonate solution and saturated brine, and then dried. Evaporation of the solvents gave a mixture of epimeric bis(tetrahydropyranyl ethers), methyl 17-(3-fluorophenyl)-9α-(4-phenylbenzoyloxy)-11α,15-bis(tetrahydropyran-2-yloxy)-18,19,20-trinorprosta-5-cis,13-trans-dien-16-ynoate, which was purified by thin layer chromatography, eluting with 15% ethyl acetate in toluene, $R_F = 0.49$ (15% ethyl acetate in toluene).

To a solution of the epimeric bis(tetrahydropyranyl ethers) (120 mg.) in 1,2-dimethoxyethane (3 ml.) was added a solution of potassium hydroxide (200 mg.) in water (2 ml.) and then methanol (about 3 ml.) was added until a homogeneous solution was obtained. The solution was stirred for 16 hours, the solvents were evaporated, and the residue was partitioned between ethyl acetate and aqueous sodium hydrogen tartrate. The ethyl acetate layer was separated, dried (magnesium sulphate), the solvent was evaporated, and the residue was purified by thin layer chromatography (two elutions with ethyl acetate) to give 17-(3-fluorophenyl)-9α-hydroxy-11α,15-bis-(tetrahydropyran-2-yloxy)-18,19,20-trinorprosta-5-cis,13-trans-dien-16-ynoic acid, $R_F = 0.33$ (ethyl acetate).

To a solution of 17-(3-fluorophenyl)-9α-hydroxy-11α,15-bis(tetrahydropyran-2-yloxy)-18,19,20-trinorprosta-5-cis,13-trans-dien-16-ynoic acid (56mg.) in acetone (2.5 ml.) at −10° C. was added Jones' reagent (chromic acid in acetone; 0.025 ml, of 8N), and after 15 minutes a further portion (0.025 ml.) of Jones' reagent was added. After a further period of 15 minutes, excess isopropanol was added, and the solvent was evaporated. The residue was partitioned between ethyl acetate and aqueous sodium hydrogen tartrate, the ethyl acetate layer was separated and dried (magnesium sulphate), and the solvent was evaporated. The residue was purified by thin layer chromatography (elution with ethyl acetate) to give 17-(3-fluorophenyl)-9-oxo-11α,15-bis(tetrahydropyran-2-yloxy)-18,19,20-trinorprosta-5-cis, 13-trans-dien-16-ynoic acid, $R_F = 0.58$ (ethyl acetate).

EXAMPLE 5

The process described in Example 2 was repeated using methyl 17-(3-fluorophenyl)-15-hydroxy-9α,11α-bis(4-phenylbenzoyloxy)-18,19,20-trinorprost-5-cis-en-16-ynoate as the starting material, to give 9α,11α,15-trihydroxy-17-(3-fluorophenyl)-18,19,20-trinorprost-5-cis-en-16-ynoic acid, mixed C-15 epimers, $R_F = 0.51$ (3% acetic acid in ethyl acetate). The mass spectrum of the tetra(trimethylsilyl) derivative showed $M^+ = 692.3554$, (calculated for $C_{35}H_{61}FO_5Si_4 = 692.3581$); n.m.r. spectrum in deuterioacetone (δ values):

7.0 – 7.55, 4H, multiplet, aromatic protons,
4.8 – 5.9, 6H, multiplet, cis-olefinic labile protons,
4.6, 1H, multiplet, C-15 proton,
3.8 – 4.24, 2H, multiplet, C-9 and C-11 protons The starting material was prepared as follows:

To a solution of methyl 17-(3-fluorophenyl)-15-oxo-9α,11α-bis(4-phenylbenzoyloxy)-18,19,20 trinorprosta-5-cis,13-trans-dien-16-ynoate (150 mg.) in a mixture of isopropanol (5 ml.) and 1,2-dimethoxyethane (10 ml.) was added sodium borohydride (8 mg.). After 30 minutes, the solution was adjusted to pH 6 with glacial acetic acid and the solvents were evaporated. The residue was partitioned between ethyl acetate and brine, the ethyl acetate layer was separated and the aqueous layer was extracted with two more portions of ethyl acetate. The combined ethyl acetate extracts were dried and the solvent was evaporated to give crude methyl 15-hydroxy-17-(3-fluorophenyl)-9α,11α-bis(4-phenylbenzoyloxy)-18,19,20-trinorprosta-5-cis-en-16-ynoate, $R_F = 0.24$ (15% ethyl acetate in toluene).

EXAMPLE 6

A solution of 9α,11α,15-trihydroxy-17-[3-(tetrahydropyran-2-yloxy)phenyl]-18,19,20-trinorprosta-5-cis,13-trans-dien-16-ynoic acid (53 mg.) in 2 ml. of a mixture of 2:1 acetic acid : water was stirred at ambient temperature for 2 hours. The solvents were evaporated and the residue was subjected to thin layer chromatography, eluting with 3% acetic acid in ethyl acetate, to give the C-15 epimers of 9α,11α,15-trihydroxy-17-(3-hydroxyphenyl)-18,19,20-trinorprosta-5-cis,13-trans-dien-16-ynoic acid, $R_F$ = 0.36 and 0.43 (3% acetic acid in ethyl acetate). The mass spectrum of the penta (trimethylsilyl)derivative showed M$^+$ = 760.3833, (calculated for $C_{38}H_{68}O_6Si_5$ = 760.3863). The n.m.r. spectrum in deuterioacetone showed the following characteristic peaks (δ values):

| | |
|---|---|
| 6.7 – 7.4, 4H, multiplet, aromatic protons, | |
| 5.7 – 5.9, 2H, multiplet, trans-olefinic protons, | |
| 5.3 – 5.6, 2H, multiplet, cis-olefinic protons, | 12 protons |
| 5.0 – 5.1, 1H, multiplet, C-15 proton, | |
| 3.6 – 6.2, broad signal, C-9, C-11 labile protons (5) | |

EXAMPLE 7

The process described in Example 2 was repeated using methyl 11α,15-dihydroxy-17-phenyl-9α-(4-phenylbenzoyloxy)-18,19,20-trinorprosta-5-cis-13-trans-dien-16-ynoate in place of methyl 17-(3-fluorophenyl)-15-hydroxy-9α,11α-di-(4-phenylbenzoyloxy)-18,19,20-trinorprosta-5-cis-13-trans-dien-16-ynoate, to give the C-15 epimers of 9α,11α,15-trihydroxy-17-phenyl-18,19,20-trinorprosta-5-cis-13-trans-dien-16-ynoic acid, $R_F$=0.27 and 0.37 (3% acetic acid in ethyl acetate.) The mass spectrum of the more polar epimer [tetra(trimethylsilyl) derivative] showed M$^+$ = 672.3464, (calculated for $C_{35}H_{60}O_5Si_4$ = 672.3519). The n.m.r. spectrum in deuterioacetone showed the following characteristic absorptions (δ values):

7.2 – 7.5, 5H, multiplet, aromatic protons,
5.6 – 5.8, 2H, multiplet, trans-olefinic protons,
5.1 – 5.6, 2H, multiplet, cis-olefinic protons,
4.95–5.05, 1H, C-15 proton The starting material for the above process was prepared by the process described in the second part of Example 3, using methyl 7-[2β-formyl-3α-hydroxy-5α-(4-phenylbenzoyloxy)cyclopent-1α-yl]hept-5-cis-enoate in place of methyl 7-[2β-formyl-3α-hydroxy-5α-(4-phenylbenzoyloxy)cyclopent-1α-yl]heptanoate, and dimethyl 2-oxo-4-phenylbut-3-ynylphosphonate in place of dimethyl 4-(3-methoxyphenyl)-2-oxobut-3-ynylphosphonate, to give methyl 11α-hydroxy-15-oxo-17-phenyl-9α-(4-phenylbenzoyloxy)-18,19,20-trinorprosta-5-cis,13-trans-dien-16-ynoate, $R_F$ = 0.33 (ether), n.m.r. in deuteriochloroform (δ values):

| | | |
|---|---|---|
| 8.15, | 2H, doublet (J = 8Hz) | C-13 and aromatic protons, |
| 7.05 – 7.8, | 13H, multiplet | |
| 6.5, | 2H, doublet (J = 16 Hz), C-14 proton, | |
| 5.2 – 5.6, | 3H, multiplet, cis olefinic protons, | |
| 4.1 – 4.4, | 1H, multiplet, C-9 proton, | |
| 3.56, | 3H, singlet, methyl ester | | which was reduced by the process described in the latter part of Example 1 to the C-15 epimers of methyl 11α,15-dihydroxy-17-phenyl-9α-(4-phenylbenzoyloxy)- 18,19,20-trinorprosta-5-cis,13-trans-dien-16-ynoate, $R_F$ = 0.51 and 0.61 (ethyl acetate).

EXAMPLE 8

The process described in Example 2 was repeated using methyl 17-(3-fluorophenyl)-15-hydroxy-15-methyl-9α,11α-bis-(4-phenylbenzoyloxy)-18,19,20-trinorprosta-5-cis,13-trans-dien-16-ynoate in place of methyl 17-(3-fluorophenyl)-15-hydroxy-9α,11α-bis-(4-phenylbenzoyloxy)-18,19,20-trinorprosta-5-cis,13-trans-dien-16-ynoate, to give the C-15 epimers of 17-(3-fluorophenyl)-9α,11α,15-trihydroxy-15-methyl-18,19,20-trinorprosta-5-cis,13-trans-dien-16-ynoic acid, $R_F$=0.30 and 0.36 (3% acetic acid in ethyl acetate). The mass spectrum of the tetra(trimethylsilyl) derivative showed M$^+$ = 704.3518 (calculated for $C_{36}H_{61}FO_5Si_4$ = 704.3581).

The methyl 17-(3-fluorophenyl)-15-hydroxy-15-methyl-9α,11α-bis(4-phenylbenzoyloxy)-18,19,20-trinorprosta-5-cis,13-trans-dien-16-ynoate used as starting material in the above process may be obtained as follows:

To a solution of methyl 17-(3-fluorophenyl)-15-oxo-9α,11α-bis(4-phenylbenzoyloxy)-18,19,20-trinorprosta-5-cis,13-trans-dien-16-ynoate (168 mg.) in dry tetrahydrofuran (7 ml.) was added a solution of methylmagnesium iodide in diethyl ether (63.5 μl.; 3.4 M), and the solution was stirred for ½ hour. More methylmagnesium iodide (63.5 μl.; 3.4 M) was added, and stirring was continued. After ½ hour, saturated aqueous sodium hydrogen tartrate, brine and ethyl acetate were added. The organic phase was separated and dried, and the solvents were evaporated. Preparative thin layer chromatography gave methyl 17-(3-fluorophenyl)-15-hydroxy-15-methyl-9α,11α-bis(4-phenylbenzoyloxy)-18,19,20-trinorprosta-5-cis,13-trans-dien-16-ynoate, $R_F$=0.28 (15% ethyl acetate in toluene). The n.m.r. spectrum in deuterioacetone showed the following characteristic absorptions (δ values):

7.1 – 8.3, 22H, multiplet, aromatic protons,
6.22, 1H, double doublet (J=15 Hz, J$^1$=7 Hz), C-13 proton,
5.98, 1H, doublet (J = 15 Hz), C-14 proton,
5.2 – 5.7, 4H, multiplet, C-9, C-11 and cis olefinic protons,
3.51, 3H, singlet, methyl ester,
1.62, 3H, singlet, methyl at C-15

EXAMPLE 9

A mixture of C-15 epimers of 17-(2-fluorophenyl)-9α,11α,15-tri(tetrahydropyran-2-yloxy)-18,19,20-trinorprosta-5-cis,13-trans-dien-16-yn-1-ol was dissolved in 2 ml. of a mixture of 2:1 acetic acid:water, and the solution was stirred at ambient temperature for 2 hours. The solvents were evaporated, and the residue was purified by thin layer chromatography to give the C-15 epimers of 17-(2-fluorophenyl)-9α,11α,15-trihydroxy-18,19,20-trinorprosta-5-cis,13-trans-dien-16-yn-1-ol, $R_F$ = 0.3

(3% acetic acid in ethyl acetate), M+ = 676.3608, (calculated for $C_{35}H_{61}FO_4Si_5$ = 676.3631).

The starting material for the above process was prepared as follows:

To a solution of the epimeric diols (15 mg.), 17-(2-fluorophenyl)-9α,11α,15-trihydroxy-18,19,20-trinorprosta-5-cis,13-trans-dien-16-ynoic acid, in methylene dichloride (1 ml.) at 0° C. under an atmosphere of argon were added successively redistilled 2,3-dihydropyran (25 mg.) and a solution of toluene-p-sulphonic acid (7 μl. of 1% solution in anhydrous tetrahydrofuran). After 20 minutes the solution was worked-up by the process described in Example 4, to give crude tetrahydropyran-2-yl 17-(2-fluorophenyl)-9α,11α,15-tris(tetrahydropyran-2-yloxy)-18,19,20-trinorprosta-5-cis,13-trans-dien-16-ynoate, $R_F$ = 0.84 (3% glacial acetic acid in ethyl acetate).

The crude tetrakis (tetrahydropyran-2-yl) derivative (45 mg.) was dissolved in anhydrous tetrahydrofuran (2 ml.) and an excess of lithium aluminium hydride was added. The mixture was stirred under argon at ambient temperature for 45 minutes, then water was added to destroy the excess of reducing agent, and the mixture was extracted with ethyl acetate. The organic extract was separated and dried, and the solvent was evaporated to give a crude mixture of C-15 epimers of 17-(2-fluorophenyl)-9α,11α,15-tri(tetrahydropyran-2-yloxy)-18,19,20-trinorprosta-5-cis,13-trans-dien-16-yn-1-ol, used as starting material without purification.

EXAMPLE 10

17-(3-Fluorophenyl)-9α,11α,15α-trihydroxy-18,19,20-trinorprosta-5-cis,13-trans-dien-16-ynoic acid: 250 μg.

Sodium citrate B.P.: 30.5 mg.
Citric acid, anhydrous, B.P.: 2.8 mg.
Sodium chloride, Ph.Eur.: 35.0 mg.
Water for injections, Ph.Eur. to : 5.0 ml.

The sodium citrate, citric acid and sodium chloride are dissolved in most of the water, the 17-(3-fluorophenyl)-9α,11α,15α-trihydroxy-18,19,20-trinorprosta-5-cis,13-trans-dien-16-ynoic acid is added, and the solution is made up to volume with water for injections. The solution is filtered to remove particulate matter, filled into neutral glass ampoules and autoclaved, to give an injectable pharmaceutical or veterinary composition.

What we claim is:

1. A prostanoic acid derivative of the formula:

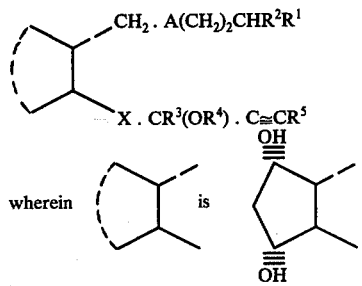

$R^1$ is carboxy or alkoxycarbonyl of 2 to 12 carbon atoms, A is ethylene or vinylene, X is ethylene or trans-vinylene, $R^2$, $R^3$ and $R^4$ which may be the same or different are each hydrogen or alkyl of 1 to 5 carbon atoms and $R^5$ is phenyl or naphthyl, which is unsubstituted or is substituted by alkyl, alkoxy or halogenoalkyl each of 1 to 5 carbon atoms, halogen, or hydroxy and for those derivatives wherein $R^1$ is carboxy the pharmaceutically or veterinarily acceptable base addition salts thereof.

2. The prostanoic acid derivative of claim 1 wherein $R^1$ is carboxy or alkoxycarbonyl of 2 to 5 carbon atoms, A is cis-vinylene, X is ethylene or trans-vinylene, $R^2$ and $R^4$ are hydrogen, $R^3$ is hydrogen or alkyl of 1 to 5 carbon atoms, and $R^5$ is phenyl which is unsubstituted or bears one substituent selected from chlorine, fluorine, methyl, methoxy and trifluoromethyl.

3. the prostanoic acid derivative of claim 2 wherein $R^1$ is carboxy or methoxycarbonyl, $R^2$ and $R^4$ are each hydrogen, $R^3$ is hydrogen or methyl, A is cis vinylene, X is trans-vinylene, and $R^5$ is phenyl, 2-, 3- or 4-chlorophenyl, 2-, 3- or 4-fluorophenyl, 3-trifluoromethylphenyl, 2- or 3-tolyl.

4. The prostanoic acid derivative of claim 1 which is 9α,11α,15-trihydroxy-17-phenyl-18,19,20-trinorprosta-5-cis,13-trans-dien-16-ynoic acid, methyl 9α,11α,15-trihydroxy-17-phenyl-18,19,20-trinorprosta-5-cis,13-trans-dien-16-ynoate, 17-(3-fluorophenyl)-9α,11α,15-trihydroxy-18,19,20-trinorprosta-5-cis,13-trans-dien-16-ynoic acid or 17-(3-fluorophenyl)-9α,11α,15-trihydroxy-15-methyl-18,19,20-trinorprosta-5-cis,13-trans-dien-16-ynoic acid.

5. The prostanoic acid derivative of claim 1 which is 17-(3-fluorophenyl)-9α,11α,15-trihydroxy-18,19,20-trinorprosta-5-cis,13-trans-dien-16-ynoic acid.

6. A pharmaceutical or veterinary composition comprising the prostanoic acid derivative of claim 1 and a major amount of a pharmaceutically or veterinarily acceptable diluent or carrier therefor.

7. A method of inducing luteolysis in a mammalian host requiring such treatment which comprises administering to said host a luteolytically effective amount of the prostanoic acid derivative of claim 1.

* * * * *